(12) United States Patent
Corradi et al.

(10) Patent No.: US 8,716,545 B1
(45) Date of Patent: May 6, 2014

(54) METHODS AND APPARATUSES FOR SEPARATING TOLUENE FROM MULTIPLE HYDROCARBON STREAMS

(71) Applicant: UOP LLC, Des Plaines, IL (US)

(72) Inventors: Jason T. Corradi, Arlington Heights, IL (US); David William Ablin, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/712,714

(22) Filed: Dec. 12, 2012

(51) Int. Cl.
*C07C 7/04* (2006.01)

(52) U.S. Cl.
USPC .............................. 585/806; 585/805; 585/802

(58) Field of Classification Search
None
See application file for complete search history.

(56) References Cited

U.S. PATENT DOCUMENTS

| | | | |
|---|---|---|---|
| 4,306,107 A | 12/1981 | Broughton | |
| 4,864,069 A | 9/1989 | Zinnen | |
| 5,017,735 A | 5/1991 | Fellmann et al. | |
| 5,177,295 A | 1/1993 | Oroskar et al. | |
| 5,912,395 A | 6/1999 | Noe | |
| 6,369,287 B1 | 4/2002 | Magne-Drisch et al. | |
| 6,395,951 B1 * | 5/2002 | Hamm | 585/827 |
| 6,448,459 B1 | 9/2002 | Magne-Drisch et al. | |
| 7,267,746 B1 * | 9/2007 | Harris et al. | 202/160 |
| 2006/0287563 A1 * | 12/2006 | Schultz et al. | 585/481 |
| 2009/0324457 A1 * | 12/2009 | Bresler et al. | 422/187 |
| 2013/0225838 A1 * | 8/2013 | Lee et al. | 549/87 |

OTHER PUBLICATIONS

"m-Xylene Gets a Market Boost", Chemical Engineering, v 106, n 12, p. 96, Nov. 1999.
Corradi, U.S. Appl. No. 13/327,029, filed Dec. 15, 2011.
Corradi et al., U.S. Appl. No. 13/626,191, filed Sep. 25, 2012.

* cited by examiner

*Primary Examiner* — Tam M Nguyen
(74) *Attorney, Agent, or Firm* — Mark R Willis

(57) ABSTRACT

Methods and apparatuses for separating toluene from multiple hydrocarbon streams are provided. A method includes fractionating a first hydrocarbon stream, which includes benzene-depleted fractionation bottoms from benzene fractionation, in a first fractionation zone into a first fractionation overhead stream that includes toluene and a first fractionation bottoms. A second hydrocarbon stream, which includes toluene and is substantially free of compounds having a higher vapor pressure than toluene, is fractionated in a second fractionation zone into a second fractionation overhead stream including toluene and a second fractionation bottoms. The second fractionation zone is in liquid isolation from and in vapor communication with the first fractionation zone. The first fractionation bottoms are removed from the first fractionation zone, and the second fractionation bottoms are removed from the second fractionation zone separate from the first fractionation bottoms. The first fractionation overhead stream and the second fractionation overhead stream are combined to produce a combined fractionation overhead stream.

19 Claims, 2 Drawing Sheets

METHODS AND APPARATUSES FOR SEPARATING TOLUENE FROM MULTIPLE HYDROCARBON STREAMS

TECHNICAL FIELD

Figure 1:
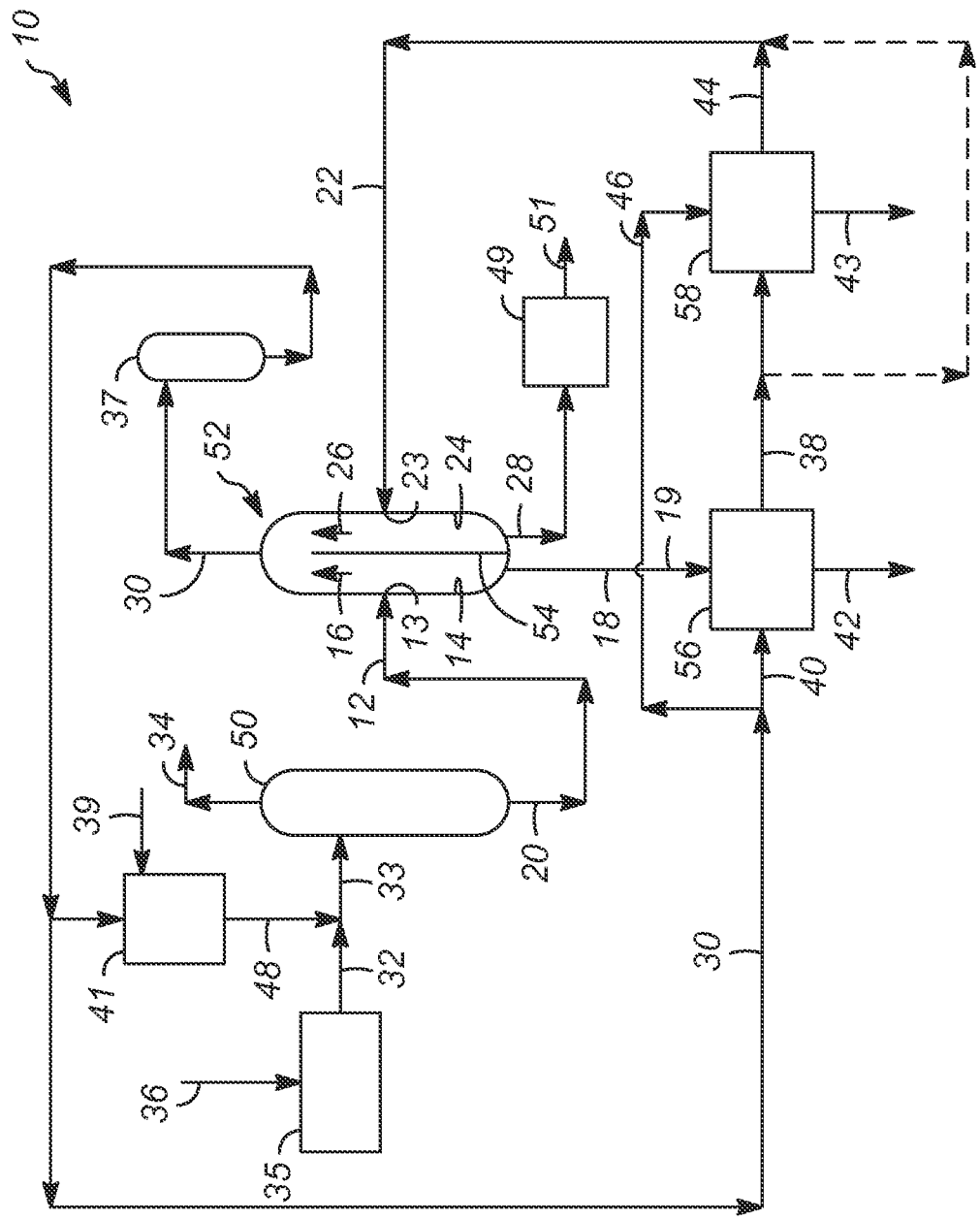

The technical field generally relates to methods and apparatuses for separating toluene from hydrocarbon streams that include the toluene, and more particularly relates to methods and apparatuses for separating toluene from different hydrocarbon streams that include toluene.

BACKGROUND

Aromatic compounds have a multitude of uses, both as end products and as reactants for downstream processes. Methods of preparing aromatic compounds from a hydrocarbon feed are generally known in the art and include upgrading the hydrocarbon feed followed by reforming and aromatics separation. Typical upgrading techniques include hydrotreating to remove contaminants such as sulfur, nitrogen, and oxygen. After upgrading, the hydrocarbon feed is reformed in the presence of a catalyst to convert paraffins and naphthenes to a reformate that includes aromatic compounds such as xylenes, benzene, and toluene. A series of separation techniques are employed to separate the various aromatic compounds from the reformate, and numerous product streams having varying degrees of purity may be isolated for each aromatic compound in the reformate.

Toluene is a common aromatic compound that has many uses not only as an end product, but also as a process stream during production of other aromatic compounds. Toluene is generally separated from a reformate in a toluene column that is downstream of a benzene column. The toluene column fractionates benzene-depleted reformate into a toluene-containing stream and a xylene-containing stream. The toluene-containing stream can be blended with C9 or greater aromatic compounds for conversion into xylenes and benzene through disproportionation and transalkylation. The xylenes and benzene produced through disproportionation and transalkylation can be separated along with the reformate through conventional separation techniques.

Adsorption/desorption is a common separation technique that is employed for separation of xylene isomers, such as para-xylene, meta-xylene, and ortho-xylene. During adsorption/desorption, select xylene isomers, such as para-xylene or meta-xylene, are adsorbed from a xylene-containing stream that is generally depleted of benzene and toluene. Specific xylene isomers can be selectively adsorbed by selecting appropriate adsorbing material. A desorbent, which can be readily separated from adsorbed compounds through fractionation, is generally employed to remove adsorbed isomers from the adsorbent material. Raffinate from adsorption/desorption generally also includes the desorbent, and the desorbent is generally separated from the raffinate through fractionation to recover the desorbent for further use.

Due to different compositional makeup of the raffinate and the reformate, the raffinate and the reformate are generally fractionated through separate fractionation techniques to separate individual compounds therefrom. Separate fractionation is conducted even when a desorbent such as toluene is used and is present in the raffinate. For example, whereas the reformate can be fractionated in the toluene fractionation unit to produce a bottoms stream that includes a range of xylene isomers, the raffinate from adsorption/desorption is generally depleted of para- and/or meta-xylenes such that mixing of the raffinate with the reformate would dilute the content of para- and/or meta-xylenes in the bottoms stream from the toluene fractionation unit. Instead, the raffinate is separately fractionated from the reformate to produce a bottoms stream that contains any xylenes that remain after adsorption/desorption, such as ortho-xylene, and the ortho-xylene may be isomerized to produce para-xylene or meta-xylene. Separate fractionation columns and associated units such as receiver vessels and overhead pumps are thus required for fractionating the reformate separate from the raffinate.

Accordingly, it is desirable to provide methods and apparatuses for separating toluene from multiple hydrocarbon streams, such as a hydrocarbon stream including reformate and a hydrocarbon stream including raffinate from para-xylene and/or meta-xylene adsorption/desorption processes, that enable duplication of fractionation equipment to be minimized. Furthermore, other desirable features and characteristics of the present invention will become apparent from the subsequent detailed description of the invention and the appended claims, taken in conjunction with the accompanying drawings and this background of the invention.

BRIEF SUMMARY

Methods and apparatuses for separating toluene from multiple hydrocarbon streams are provided. In an embodiment, a method of separating toluene from multiple hydrocarbon streams includes fractionating a first hydrocarbon stream in a first fractionation zone into a first fractionation overhead stream and a first fractionation bottom stream. The first hydrocarbon stream includes the benzene-depleted fractionation bottom stream from benzene fractionation. The first fractionation overhead stream includes toluene. A second hydrocarbon stream different from the first hydrocarbon stream is fractionated in a second fractionation zone into a second fractionation overhead stream and a second fractionation bottom stream. The second fractionation zone is in liquid isolation from and in vapor communication with the first fractionation zone. The second hydrocarbon stream includes toluene and is substantially free of compounds that have a higher vapor pressure than toluene. The second fractionation overhead stream includes toluene. The first fractionation bottom stream is removed from the first fractionation zone, and the second fractionation bottom stream is removed from the second fractionation zone separate from the first fractionation bottom stream. The first fractionation overhead stream from the first fractionation zone and the second fractionation overhead stream from the second fractionation zone are combined to produce a combined fractionation overhead stream that includes toluene.

In another embodiment, a method of separating toluene from multiple hydrocarbon streams includes providing a benzene column for receiving a benzene-containing hydrocarbon stream that includes xylenes, benzene, and toluene. The benzene-containing hydrocarbon stream is fractionated into a benzene-containing overhead stream and a benzene-depleted fractionation bottom stream that includes xylenes and toluene. A split fractionation column is provided that includes an internal partition. The internal partition defines a first fractionation zone and a second fractionation zone in liquid isolation from and in vapor communication with the first fractionation zone. A first hydrocarbon stream is fractionated in the first fractionation zone into a first fractionation overhead stream and a first fractionation bottom stream. The first hydrocarbon stream includes the benzene-depleted fractionation bottom stream from the benzene column. The first fractionation overhead stream includes toluene and the first fractionation bottom stream includes xylenes. A second hydrocarbon stream is fractionated in the second fractionation zone into a second fractionation overhead stream and a second fractionation bottom stream. The second hydrocarbon stream includes an adsorption raffinate that is depleted of at least one of para-xylene or meta-xylene, and the adsorption raffinate includes toluene. The second hydrocarbon stream is substantially free of compounds that have a higher vapor pressure than toluene. The second fractionation overhead stream includes toluene. The first fractionation bottom stream is removed from the first fractionation zone, and the second fractionation bottom stream is removed from the second fractionation zone separate from the first fractionation bottom stream. The first fractionation overhead stream from the first fractionation zone and the second fractionation overhead stream from the second fractionation zone are combined to produce a combined fractionation overhead stream including toluene.

In another embodiment, an apparatus for separating toluene from multiple hydrocarbon streams includes a benzene column, a processing unit, and a split fractionation column. The benzene column receives a benzene-containing hydrocarbon stream that includes xylenes, benzene, and toluene. The processing unit provides a second hydrocarbon stream that includes toluene and that is substantially free of compounds that have a higher vapor pressure than toluene. The split fractionation column includes an internal partition that defines a first fractionation zone and a second fractionation zone. The second fractionation zone is in liquid isolation from and in vapor communication with the first fractionation zone. The first fractionation zone is in fluid communication with the benzene column for receiving a first hydrocarbon stream that includes a benzene-depleted fractionation bottom stream from the benzene column. The second fractionation zone is in fluid communication with the processing unit for receiving the second hydrocarbon stream.

DETAILED DESCRIPTION OF THE DRAWINGS

Figure 2:
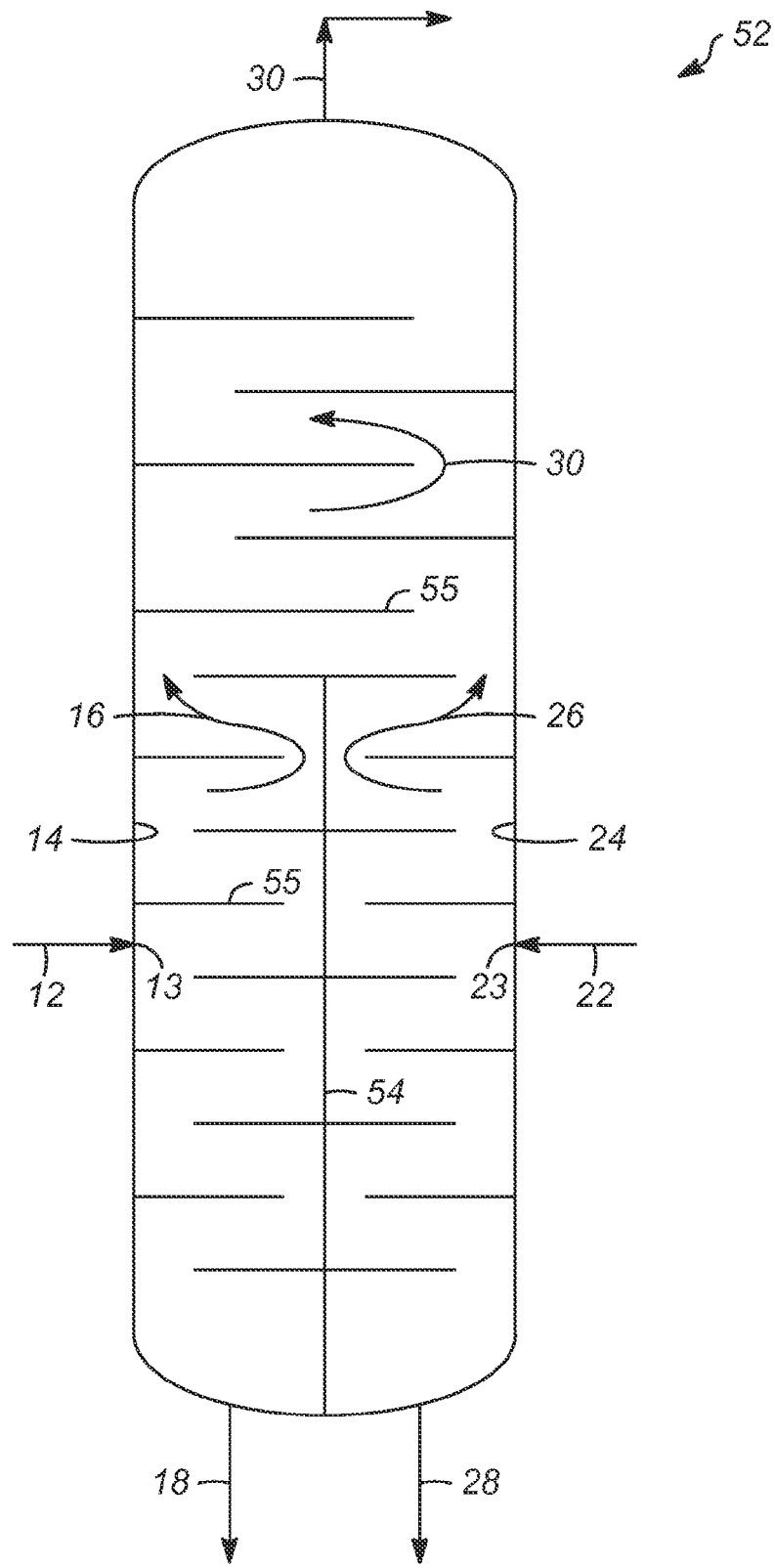

The various embodiments will hereinafter be described in conjunction with the following drawing figures, wherein like numerals denote like elements, and wherein:

FIG. 1 is a schematic diagram of an apparatus and method for separating toluene from multiple hydrocarbon streams in accordance with an exemplary embodiment; and FIG. 2 is a schematic cross-sectional side view of a split fractionation column in accordance with an exemplary embodiment.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

Methods and apparatuses for separating toluene from multiple hydrocarbon streams are provided herein. The toluene can be removed from the multiple hydrocarbon streams, which have different compositional makeups, while minimizing duplication of fractionation equipment by fractionating the individual hydrocarbon streams in respective fractionation zones that are in liquid isolation from each other, but that are also in vapor communication with each other. In this manner, fractionation overhead streams from the respective fractionation zones are combined while the fractionation bottom streams from the respective fractionation zones are kept separate, thereby at least avoiding duplication of separate overhead receivers, pumps, or other overhead-handling equipment that would otherwise be required if the fractionation overhead streams from the respective fractionation zones were to be separated. Further, a split fractionation column can be employed, with the respective fractionation zones included in the split fractionation column and separated by at least one internal partition to maintain liquid separation between the respective fractionation zones, thus avoiding duplication of separation fractionation columns for the respective fractionation zones.

In an embodiment, and as shown in FIG. 1, an apparatus 10 for separating toluene from multiple hydrocarbon streams is provided. In this embodiment, one of the hydrocarbon streams from which toluene is separated is a first hydrocarbon stream 12 that includes a benzene-depleted fractionation bottom stream 20 from benzene fractionation. It is to be appreciated that the first hydrocarbon stream 12 may include additional hydrocarbons other than those originating from the benzene-depleted fractionation bottom stream 20. In an embodiment and as shown in FIG. 1, the benzene fractionation involves a benzene column 50 that is provided for receiving a benzene-containing hydrocarbon stream 33 that includes xylenes, benzene, and toluene and for fractionating the benzene-containing hydrocarbon stream 33 to produce the benzene-depleted fractionation bottom stream 20. In particular, the benzene-containing hydrocarbon stream 33 is fractionated into a benzene-containing overhead stream 34 that includes benzene and, optionally, other hydrocarbons that have a higher vapor pressure than benzene. However, it is to be appreciated that such other hydrocarbons that have the higher vapor pressure than benzene can be removed from the benzene-containing hydrocarbon stream 33 in other fractionation units (not shown) prior to fractionation in the benzene column 50 such that the benzene-containing overhead stream 34 generally includes benzene with only trace amounts of the other hydrocarbons that have higher vapor pressure than benzene in accordance with conventional benzene fractionation. The benzene-depleted fractionation bottom stream 20 includes xylenes and toluene, and may further include any other hydrocarbons that are present in the benzene-containing hydrocarbon stream 33 and that have a lower vapor pressure than benzene.

The source of the benzene-containing hydrocarbon stream 33 is not limited. In one specific embodiment, the benzene-containing hydrocarbon stream 33 includes a reformate stream 32. The reformate stream 32 may be provided to the benzene column 50 from a source that is external to the apparatus 10 or from a source that is included in the apparatus 10. For example, in an embodiment and as shown in FIG. 1, a hydrocarbon feed 36 is reformed in an upgrading/reforming zone 35, such as in the presence of a reforming catalyst (not shown), to produce the reformate stream 32 through conventional reforming techniques. The hydrocarbon feed 36 is not limited and may include any source of hydrocarbons, such as those originating from petroleum and/or renewable sources. The upgrading/reforming zone 35 optionally includes an upgrading unit (not shown), such as a hydrotreating unit, for hydrotreating the hydrocarbon feed 36 to remove contaminants such as sulfur, nitrogen, and oxygen from the hydrocarbon feed 36 prior to reforming. It is to be appreciated that the benzene-containing hydrocarbon stream 33 may include additional hydrocarbons other than those originating from the reformate stream 32, as described in further detail below. In other embodiments, the benzene-containing hydrocarbon stream 33 only includes the reformate stream 32.

Another one of the hydrocarbon streams from which the toluene is separated is a second hydrocarbon stream 22 that is different from the first hydrocarbon stream 12. In particular, the second hydrocarbon stream 22 includes toluene and is substantially free of compounds that have a higher vapor pressure than toluene. By "substantially free", it is meant that the second hydrocarbon stream 22 is desirably free of compounds that have a higher vapor pressure than toluene, and may contain trace amounts of such compounds, such as up to about 1 wt % of such compounds based upon the total weight of the second hydrocarbons stream 22. In this regard, the toluene can be separated from the second hydrocarbon stream 22 through fractionation, with the toluene that is separated from the second hydrocarbon stream 22 combined with toluene that is separated from the first hydrocarbon stream 12, without contaminating the toluene with other compounds such that the toluene can be repurposed for other uses either as a product itself and/or as a reactant within other units within the apparatus 10.

In an embodiment and as shown in FIG. 1, the apparatus 10 includes a processing unit 56 and/or 58 for providing the second hydrocarbon stream 22. The processing unit 56 and/or 58 is not limited and can include any unit that produces the second hydrocarbon stream 22 that includes toluene and that is substantially free of compounds that have a higher vapor pressure than toluene. In an embodiment and as shown in FIG. 1, the processing unit 56 and/or 58 includes at least one adsorption unit 56, 58, which is employed for selectively adsorbing certain compounds from a hydrocarbon feed 36. For example, in an embodiment, the at least one adsorption unit 56, 58 adsorbs at least one of para-xylene or meta-xylene from a xylene-containing feed stream 19 to produce an adsorption raffinate 38, 44 that is depleted of at least one of para-xylene or meta-xylene, and the adsorption raffinate 38, 44 can be included in the second hydrocarbon stream 22. The xylene-containing feed stream 19 is not limited and can be provided from any source. In an embodiment and as described in further detail below, the xylene-containing feed stream 19 includes a first fractionation bottom stream 18 from fractionation of the first hydrocarbon stream 12 that includes the benzene-depleted fractionation bottom stream 20. Para-xylene and meta-xylene are commercially valuable products themselves. Para-xylene is used for the production of polyester fibers, resins, and films. Meta-xylene is useful for conversion to isophthalic acid that, along with terephthalic acid that is derived from para-xylene, can be converted into polyethylene terephthalate resin blends. Generally, separate adsorption units 56, 58 are employed to separate para-xylene and meta-xylene from the xylene-containing feed stream 19, and such adsorption units are known in the art. In an embodiment and as shown in FIG. 1, the apparatus 10 includes a para-xylene adsorption unit 56 for receiving the xylene-containing feed stream 19. The para-xylene adsorption unit 56 adsorbs para-xylene to produce a first adsorption raffinate 38 that is depleted of para-xylene. As also shown in FIG. 1, in an embodiment, the apparatus 10 further includes a meta-xylene adsorption unit 58. In this embodiment, the first adsorption raffinate 38 is fed to the meta-xylene adsorption unit 58 and meta-xylene is adsorbed from the first adsorption raffinate 38 to produce a second adsorption raffinate 44 that is depleted of meta-xylene and para-xylene.

The adsorbed para-xylene and/or meta-xylene in the respective adsorption units 56, 58 is desorbed with a desorbent stream 40, 46 to produce a para-xylene stream 42 and a meta-xylene stream 43, respectively. In accordance with an embodiment, the desorbent is toluene, which has a higher vapor pressure than para-xylene and meta-xylene and can be readily separated from the para-xylene and meta-xylene through fractionation. Separate desorbent streams 40, 46 are generally employed for desorbing the para-xylene and the meta-xylene, respectively. In particular, the adsorbed para-xylene can be desorbed with a first desorbent stream 40 including toluene to produce the para-xylene stream 42, and the adsorbed meta-xylene can be desorbed with a second desorbent stream 46 that includes toluene to produce the meta-xylene stream 43. The first desorbent stream 40 and the second desorbent stream 46 can be split from a common source of the toluene desorbent as shown in FIG. 1. The desorbent also dilutes the adsorption raffinate 38, 44 that remains after adsorption of the para-xylene and/or meta-xylene from the xylene-containing feed stream 19, and the adsorption raffinate 38, 44 that includes the toluene desorbent can be included in the second hydrocarbon stream 22 from which toluene is separated. In particular, the first adsorption raffinate 38 can be directly included in the second hydrocarbon stream 22, under circumstances where no meta-xylene adsorption is conducted or where a portion of the first adsorption raffinate 38 is diverted from meta-xylene adsorption. Alternatively, the second adsorption raffinate 44 is included in the second hydrocarbon stream 22, either alone or in combination with a portion of the first adsorption raffinate 38 and/or with other compounds that originate from sources other than the adsorption raffinate streams 38, 44. However, because the adsorption raffinate streams 38, 44 are already depleted of para-xylene and/or meta-xylene, it is undesirable to combine second hydrocarbon stream 22 and the first hydrocarbon stream 12 that includes the benzene-depleted fractionation bottom stream 20 (which generally has a para-xylene and/or meta-xylene content).

Referring to FIG. 1, a first fractionation zone 14 and a second fractionation zone 24 are provided for fractionating the first hydrocarbon stream 12 and the second hydrocarbon stream 22, respectively. In particular, the first hydrocarbon stream 12 is fractionated into a first fractionation overhead stream 16 and a first fractionation bottom stream 18, and the second hydrocarbon stream 22 is fractionated into a second fractionation overhead stream 26 and a second fractionation bottom stream 28. The first fractionation zone 14 is in liquid isolation from the second fractionation zone 24, but is also in vapor communication with the second fractionation zone 24, which allows for toluene that is fractionated in the overhead streams 16, 26 within the first fractionation zone 14 and the second fractionation zone 24 to be combined in a combined fractionation overhead stream 30. By "liquid isolation", it is meant that combined flow of liquid in the first fractionation zone 14 and liquid in the second fractionation zone 24 is prevented at least at a first introduction point 13 of the first hydrocarbon stream 12 into the first fractionation zone 14 and at a second introduction point 23 of the second hydrocarbon stream 22 into the second fractionation zone 24. It is to be appreciated that minor amounts of reflux including compounds that originate from first hydrocarbon stream 12 and/or the second hydrocarbon stream 22 can be re-introduced into the opposing fractionation zones 14, 24 without materially affecting downstream processing as described in further detail below.

In an embodiment and as shown in FIGS. 1 and 2, the first fractionation zone 14 and the second fractionation zone 24 are provided in a split fractionation column 52. The split fractionation column 52 includes an internal partition 54 to define the first fractionation zone 14 and the second fractionation zone 24. It is to be appreciated that, although not shown, the split fractionation column 52 may include multiple internal partitions 54 to define more than two fractionation zones therein, depending upon a number of different hydrocarbon streams that are to be fractionated to separate toluene therefrom. As shown in FIG. 2, the internal partition 54 partially divides the split fractionation column 52 to provide the first fractionation zone 14 in liquid isolation from the second fractionation zone 24, while also providing for vapor communication between the first fractionation zone 14 and the second fractionation zone 24 in a space within the split fractionation column 52 above the internal partition 54. Trays 55 are disposed in the first fractionation zone 14 and the second fractionation zone 24 to enable efficient fractionation and reflux. In an embodiment, the first hydrocarbon stream 12 and the second hydrocarbon stream 22 are introduced into the first fractionation zone 14 below a top tray within the respective fractionation zones, such as at least four trays 55 below the top tray within the respective fractionation zones and below the internal partition 54, to effectively maintain liquid separation between the first fractionation zone 14 and the second fractionation zone 24 and to avoid intermingling of liquid fractions in the first fractionation zone 14 and the second fractionation zone 24. It is to be appreciated that the split fractionation column 52 may include trays 55 above the internal partition 54, and that some intermingling of liquid fractions from the first fractionation zone 14 and the second fractionation zone 24 may occur in the trays 55 that are above the internal partition 54. However, even if the intermingled liquid fractions are included in the first fractionation bottom stream 18 or the second fractionation bottom stream 28, cross-contamination of the first fractionation bottom stream 18 and the second fractionation bottom stream 28 is insignificant and does not materially affect downstream processing of the first fractionation bottom stream 18 and the second fractionation bottom stream 28.

In an embodiment and as shown in FIG. 1, the first fractionation zone 14 is in fluid communication with the benzene column 50 for receiving the first hydrocarbon stream 12 that includes the benzene-depleted fractionation bottom stream 20 from the benzene column 50, and the second fractionation zone 24 is in fluid communication with the processing unit 56 and/or 58 for receiving the second hydrocarbon stream 22. In this embodiment, the first hydrocarbon stream 12 is fractionated in the first fractionation zone 14 into the first fractionation overhead stream 16 that includes toluene and the first fractionation bottom stream 18. The benzene-depleted fractionation bottom stream 20 is generally free of compounds that have a higher vapor pressure than toluene. As such, the first fractionation overhead stream 16 generally includes substantially pure toluene. Also, because the benzene-depleted fractionation bottom stream 20 generally includes xylenes, the first fractionation bottom stream 18 also includes xylenes because the xylenes have a lower vapor pressure than toluene and are therefore separated from the toluene in the first fractionation bottom stream 18. The second hydrocarbon stream 22 is fractionated in the second fractionation zone 24 into the second fractionation overhead stream 26 that includes toluene and the second fractionation bottom stream 28, which generally includes ortho-xylene and, optionally, ethylbenzene. Because the second fractionation zone 24 is in fluid communication with the processing unit 56 and/or 58, such as the para-xylene adsorption unit 56 and/or the meta-xylene adsorption unit 58, the second hydrocarbon stream 22 is generally depleted of para-xylene and/or meta-xylene such that separation between the first hydrocarbon stream 12 and the second hydrocarbon stream 22 is desired to avoid dilution of the first hydrocarbon stream 12. The first fractionation bottom stream 18 is removed from the first fractionation zone 14 and the second fractionation bottom stream 28 is removed from the second fractionation zone 24 separate from the first fractionation bottom stream 18 due to the different compositional makeup of the first fractionation bottom stream 18 and the second fractionation bottom stream 28.

In an embodiment, the xylenes in the first fractionation bottom stream 18 include para-xylene and/or meta-xylene. Thus, in an embodiment and as shown in FIG. 1, the xylene-containing feed stream 19 may include the first fractionation bottom stream 18, although it is to be appreciated that the xylene-containing feed stream 19 may include xylenes from sources other than the first fractionation bottom stream 18, such as from sources (not shown) that are external to the apparatus 10. Para-xylene from the first fractionation bottom stream 18 may be adsorbed in the para-xylene adsorption unit 56 to produce the first adsorption raffinate 38 that is depleted of para-xylene, and meta-xylene from the first adsorption raffinate 38 may be adsorbed in the meta-xylene adsorption unit 58 to produce the second adsorption raffinate 44 that is depleted of para-xylene and meta-xylene. The second fractionation bottom stream 28 may be further processed to convert the ortho-xylene therein into para-xylene in a recovery stream 51 such as, for example, by introducing the second fractionation bottom stream 28 into an isomerization unit 49.

The first fractionation overhead stream 16 and the second fractionation overhead stream 26 generally include substantially pure toluene, e.g., 99 wt % pure toluene based on the total weight of the fractionation overhead streams 16, 26. As such, the first fractionation overhead stream 16 and the second fractionation overhead stream 26 are combined to produce a combined fractionation overhead stream 30 that includes toluene, and combination of the first fractionation overhead stream 16 and the second fractionation overhead stream 26 avoids duplication of equipment for separate processing of the first fractionation overhead stream 16 and the second fractionation overhead stream 26. In an embodiment and as shown in FIGS. 1 and 2, the first fractionation overhead stream, 16 and the second fractionation overhead stream 26 are combined within the split fractionation column 52. However, it is to be appreciated that in other embodiments (not shown), the first fractionation overhead stream 16 and the second fractionation overhead stream 26 may be separately conveyed from the split fractionation column 52 and combined outside of the split fractionation column 52.

The combined fractionation overhead stream 30 including the toluene can be used for any purpose for which a substantially pure toluene stream is generally used, as an end product and/or as a reactant stream for other processes within the apparatus 10. In an embodiment and as shown in FIG. 1, the combined fractionation overhead stream 30 may be dried in a dryer 37. At least a portion of the toluene from the combined fractionation overhead stream 30 is converted into a conversion stream 48 that includes xylenes and benzene. For example, the portion of the toluene from the combined fractionation overhead stream 30 may be blended with C9 or greater compounds in a C9+ stream 39 and converted into xylenes and benzene through disproportionation and transalkylation in a conversion unit 41. The xylenes and benzene produced in the conversion unit 41 can be included in the benzene-containing hydrocarbon stream 33 along with the reformate stream 32. Further, as shown in FIG. 1, at least a portion of the toluene from the combined fractionation overhead stream 30 may be included in the first desorbent stream 40 and/or the second desorbent stream 46 that are used for desorption of the adsorbed para-xylene and/or meta-xylene, respectively, in the adsorption units 56, 58. Alternatively, the toluene from the combined fractionation overhead stream 30 may be provided as an independent product stream (not shown).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of separating toluene from multiple hydrocarbon streams, the method comprising:
   fractionating a first hydrocarbon stream in a first fractionation zone into a first fractionation overhead stream and a first fractionation bottom stream, wherein the first hydrocarbon stream comprises a benzene-depleted fractionation bottom stream from benzene fractionation, and wherein the first fractionation overhead stream comprises toluene;
   fractionating a second hydrocarbon stream different from the first hydrocarbon stream in a second fractionation zone into a second fractionation overhead stream and a second fractionation bottom stream, wherein the second fractionation zone is in liquid isolation from and in vapor communication with the first fractionation zone, wherein the second hydrocarbon stream comprises toluene and is substantially free of compounds having a higher vapor pressure than toluene, and wherein the second fractionation overhead stream comprises toluene;
   separately removing the first fractionation bottom stream from the first fractionation zone and the second fractionation bottom stream from the second fractionation zone; and
   combining the first fractionation overhead stream from the first fractionation zone and the second fractionation overhead stream from the second fractionation zone to produce a combined fractionation overhead stream comprising toluene.

2. The method of claim 1, further comprising fractionating a benzene-containing hydrocarbon stream comprising xylenes, benzene, and toluene into a benzene-containing overhead stream and the benzene-depleted fractionation bottom stream comprising xylenes and toluene.

3. The method of claim 2, further comprising reforming a hydrocarbon feed in the presence of a catalyst to produce a reformate stream, wherein the benzene-containing hydrocarbon stream includes the reformate stream.

4. The method of claim 3, wherein fractionating the first hydrocarbon stream comprises fractionating the first hydrocarbon stream into the first fractionation overhead stream comprising toluene and the first fractionation bottom stream comprising xylenes.

5. The method of claim 4, wherein the xylenes in the first fractionation bottom stream comprise para-xylene, and wherein the method further comprises adsorbing para-xylene from the first fractionation bottom stream to produce a first adsorption raffinate depleted of para-xylene.

6. The method of claim 5, further comprising desorbing the adsorbed para-xylene with a first desorbent stream comprising toluene to produce a para-xylene stream.

7. The method of claim 5, wherein fractionating the second hydrocarbon stream comprises fractionating at least a portion of the first adsorption raffinate in the second fractionation zone.

8. The method of claim 5, wherein the xylenes in the first fractionation bottom stream further comprise meta-xylene, and wherein the method further comprises adsorbing meta-xylene from the first adsorption raffinate to produce a second adsorption raffinate depleted of meta-xylene and para-xylene.

9. The method of claim 8, further comprising desorbing the adsorbed meta-xylene with a second desorbent stream comprising toluene.

10. The method of claim 8, wherein fractionating the second hydrocarbon stream comprises fractionating at least a portion of the second adsorption raffinate in the second fractionation zone.

11. The method of claim 1, wherein the second hydrocarbon stream comprises an adsorption raffinate depleted of at least one of para-xylene or meta-xylene and comprising toluene, and wherein fractionating the second hydrocarbon stream comprises fractionating the second hydrocarbon stream into the second fractionation overhead stream comprising toluene.

12. The method of claim 11, further comprising adsorbing at least one of para-xylene or meta-xylene from a xylene-containing feed stream.

13. The method of claim 12, further comprising desorbing the adsorbed para-xylene and/or meta-xylene with a desorbent stream comprising toluene.

14. The method of claim 13, wherein desorbing the adsorbed para-xylene and/or meta-xylene comprises desorbing the adsorbed para-xylene and/or meta-xylene with the desorbent stream comprising at least a portion of the toluene from the combined fractionation overhead stream.

15. The method of claim 1, further comprising converting at least a portion of the toluene from the combined fractionation overhead stream into a conversion stream comprising xylenes and benzene.

16. The method of claim 15, wherein fractionating the first hydrocarbon stream comprises fractionating the first hydrocarbon stream comprising at least a portion of the conversion stream.

17. A method of separating toluene from multiple hydrocarbon streams, the method comprising:
   providing a benzene column for receiving a benzene-containing hydrocarbon stream comprising xylenes, benzene, and toluene;
   fractionating the benzene-containing hydrocarbon stream into a benzene-containing overhead stream and a benzene-depleted fractionation bottom stream comprising xylenes and toluene;
   providing a split fractionation column comprising an internal partition defining a first fractionation zone and a second fractionation zone in liquid isolation from and in vapor communication with the first fractionation zone;
   fractionating a first hydrocarbon stream in the first fractionation zone into a first fractionation overhead stream and a first fractionation bottom stream, the first hydrocarbon stream comprising the benzene-depleted fractionation bottom stream from the benzene column, wherein the first fractionation overhead stream comprises toluene and the first fractionation bottom stream comprises xylenes;
   fractionating a second hydrocarbon stream in the second fractionation zone into a second fractionation overhead stream and a second fractionation bottom stream, the second hydrocarbon stream comprising an adsorption raffinate depleted of at least one of para-xylene or meta-xylene and comprising toluene, wherein the second hydrocarbon stream is substantially free of compounds having a higher vapor pressure than toluene, and wherein the second fractionation overhead stream comprises toluene;

separately removing the first fractionation bottom stream from the first fractionation zone and the second fractionation bottom stream from the second fractionation zone; and combining the first fractionation overhead stream from the first fractionation zone and the second fractionation overhead stream from the second fractionation zone to produce a combined fractionation overhead stream comprising toluene.

18. The method of claim 17, wherein the first fractionation zone and the second fractionation zone are in vapor communication within the split fractionation column, and wherein combining the first fractionation overhead stream and the second fractionation overhead stream comprises combining the first fractionation overhead stream and the second fractionation overhead stream within the split fractionation column.

19. The method of claim 17, further comprising providing at least one adsorption unit for adsorbing at least one of para-xylene or meta-xylene from a xylene-containing feed stream, where the xylene-containing feed stream comprises the first fractionation bottom stream.

\* \* \* \* \*